(12) United States Patent
Hu

(10) Patent No.: US 8,557,594 B2
(45) Date of Patent: Oct. 15, 2013

(54) METHOD FOR DETERMINING CHROMIUM CONTENT IN A TUNGSTEN MATRIX WITH ADDED CHROMIUM OR SIMULTANEOUSLY ADDED CHROMIUM AND VANADIUM

(75) Inventor: Yiqi Hu, Jiangxi (CN)

(73) Assignee: JiangXi Rare Earth And Rare Metals Tungsten Group Corporation, Jiangxi (CN)

( * ) Notice: Subject to any disclaimer, the term of this patent is extended or adjusted under 35 U.S.C. 154(b) by 78 days.

(21) Appl. No.: 13/139,032

(22) PCT Filed: Dec. 9, 2009

(86) PCT No.: PCT/CN2009/075418
§ 371 (c)(1),
(2), (4) Date: Aug. 3, 2011

(87) PCT Pub. No.: WO2010/066190
PCT Pub. Date: Jun. 17, 2010

(65) Prior Publication Data
US 2011/0300634 A1    Dec. 8, 2011

(30) Foreign Application Priority Data
Dec. 12, 2008   (CN) .......................... 2008 1 0239821

(51) Int. Cl.
*G01N 33/20*    (2006.01)
(52) U.S. Cl.
USPC .......................................................... 436/83
(58) Field of Classification Search
USPC ........... 436/84, 83; 423/55, 92, 122, 131, 140
See application file for complete search history.

(56) References Cited

U.S. PATENT DOCUMENTS

| 2,960,387 A * | 11/1960 | Wainer | 423/84 |
| 4,305,754 A * | 12/1981 | Rappas et al. | 75/419 |
| 4,798,708 A * | 1/1989 | Ladd et al. | 423/55 |
| 2004/0086438 A1 * | 5/2004 | Sreeram et al. | 423/55 |

OTHER PUBLICATIONS

Amperometric Microtitration of Very Dilute Chromate Solutions Industrian and Engineering Chemistry vol. 18, No. 3 I. M. Kolthoff and D. R. May.*
Chemical Analysis of Ferrous Materials, Determination of Chromium in Steels and Irons, Method by Potentiometric and Visual Titration Euronorm Dec. 1980.*

* cited by examiner

*Primary Examiner* — Krishnan S Menon
*Assistant Examiner* — Dwan A Gerido
(74) *Attorney, Agent, or Firm* — Hammer & Associates, P.C.

(57) ABSTRACT

A method for determining chromium content in a tungsten matrix with singly or simultaneously added chromium and vanadium, characterized in that a test sample is subjected to melting with sodium peroxide and hot water leaching; meanwhile said sodium peroxide is also used as an oxidizing agent to oxidize all the chromium to high valences; the main body of tungsten is coordinated by ammonium hydrogen fluoride to prevent tungstic acid from precipitating; precipitation and turbidity are avoided throughout the analysis, titration can be carried out in a quite clear condition with accurate and reliable results. In this invention, the clearness of the solution when titrating is very important for the accuracy of titrimetric analysis; the solution is always clear throughout the determination, ensuring that the interference with determination of chromium from vanadium is accurately and quantitatively eliminated; the interference from vanadium is eliminated by subtraction method, by means of titrating with ferrous ammonium sulfate standard solution after oxidation with potassium permanganate. In this invention, the determination method allows the determination to be carried out in the quite clear condition, and eliminates the interference from vanadium completely and quantitatively, thus the accuracy and speed of the determination of chromium content in a tungsten matrix with singly or simultaneously added chromium and vanadium are improved.

10 Claims, No Drawings

METHOD FOR DETERMINING CHROMIUM CONTENT IN A TUNGSTEN MATRIX WITH ADDED CHROMIUM OR SIMULTANEOUSLY ADDED CHROMIUM AND VANADIUM

TECHNICAL FIELD

The present invention relates to a method for determining chromium content in a tungsten matrix with added chromium or simultaneously added chromium and vanadium.

The term "optimization of conditions for analysis" herein refers to a novel redox system, which successfully allows the classical redox titration applicable to the accurate macroanalysis of chromium in a tungsten system, the method is simple, accurate and fast. Meanwhile, by the optimization of conditions for analysis, the mutual interference between chromium and vanadium in the analysis can be accurately and quantitatively eliminated, the accurate measurement of chromium and vanadium contents in a tungsten matrix with simultaneously added chromium and vanadium can be done.

The term "matrix" herein is also referred to as "medium" or "base material".

The term "tungsten matrix" herein refers to a sample for analysis, in which all the materials and components except the analytes are tungsten, such as tungsten carbide and the like.

PRIOR ART

In production of fine or ultra-fine particulate tungsten carbide powders, it is often necessary to add chromium and vanadium compounds separately or simultaneously. There are no such macroanalytical methods for chromium and vanadium in the existing analytical methods. And as there is interference between chromium and vanadium, it is more difficult to measure the contents of chromium and vanadium accurately in simultaneous addition of chromium and vanadium. In tungsten industry, large companies typically carry out the simultaneous determination the contents of chromium and vanadium, etc. by means of X-ray fluorescence analyzer; and the method is fast and accurate. However, the price of the X ray fluorescence analyzer is up to millions of RMB Yuan or more, therefore, small and medium-sized enterprises generally do not have such high-end test equipments.

Most enterprises utilize classical redox titration for the macroanalysis of chromium in a tungsten system, that is, in an acidic medium, silver nitrate is used as the catalyst, a manganese salt is used as indicator, ammonium persulfate is used as the oxidizing agent to oxidize the low valent chromium, sodium chloride is used to attack high valent manganese, and the chromium content is determined by titration with ferrous standard solution.

The method for determining chromium content in a tungsten matrix with singly added chromium by classical redox titration is as follows:

1. Scope

This method is suitable for determining chromium content in a tungsten matrix with singly added chromium, and measuring range is 0.05-1.00%.

2. Principle

A sample is dissolved with sulfuric acid and ammonium sulfate, and is oxidized with ammonium persulfate in a sulfuric acid medium, using silver nitrate as catalyst, then the chromium is titrated with ferrous standard solution.

3. Reagent:

3.1 Ammonium sulfate AR 3.2 Phosphoric acid AR, ($\rho$1.68)

3.3 Silver nitrate solution AR, 1.00%

3.4 Sulfuric acid AR, ($\rho$1.84)

3.5 Nitric acid AR, ($\rho$1.42)

3.6 Manganese sulfate solution AR, 1.00%

3.7 Ammonium persulfate AR 3.8 o-Anilinobenzoic acid AR, 0.20%

3.9 Sodium chloride solution AR, 2.50%

3.10 Mixed acid solution of sulfuric acid and phosphoric acid (15+15+75) AR 3.11 Sodium diphenylaminesulfonate AR, (2 g/L)

3.12 Potassium dichromate standard solution: AR, c ($\frac{1}{6}K_2Cr_2O_7$)=0.05 mol/L.

3.13 Ferrous standard solution 3.13.1 Preparation: Weighing 60 g ferrous ammonium sulfate and dissolving it in 2000 ml water, adding 250 ml sulfuric acid (3.4) and cooling, diluting with water to 5000 ml and shaking well.

3.13.2 Calibration: Pipetting 20 ml solution (3.13.1) to a 500 ml Erlenmeyer flask, adding 100 ml of water, adding 15 ml mixed acid solution of sulfuric acid and phosphoric acid (3.10), shaking well, adding 2 drops of sodium diphenylaminesulfonate (3.11) as indicator, and titrating with potassium dichromate standard solution (3.12) to the point where the solution shows a stable purple red color.

Calculation: the standard concentration of the ferrous solution is calculated according to the following equation.

$$c[FeSO_4 \cdot (NH_4)_2SO_4] = \frac{c_1(1/6K_2Cr_2O_7) \cdot V_1}{V_2}$$

Wherein:

$c_1$ is the concentration of potassium dichromate standard solution, mol/L;

$V_1$ is the volume of potassium dichromate standard solution consumed, ml; and $V_2$ is the volume of ferrous ammonium sulfate solution pipetted, ml.

4. Sample

Crushing in a mortar that does not change the composition of the sample and passing through screen meshes with hole diameter of 0.18 mm.

5. Analytical procedure 5.1 The number of measurement

Weighing two samples for the measurement.

5.2 Sample weight

Weighing 0.4 g of sample being accurate to 0.0001 g.

5.3 Measurement 5.3.1 Placing a sample (5.2) in a 500 ml Erlenmeyer flask, adding 8 g ammonium sulfate (3.1), 12 ml sulfuric acid (3.4) and 5 ml nitric acid (3.5), heating in an electric furnace to dissolve completely, and removing it and cooling.

5.3.2 diluting with water to 200 ml, adding 5 ml sulfuric acid (3.4), 5 ml phosphoric acid (3.2), 1 to 2 drops of manganese sulfate solution (3.6) and 3 ml silver nitrate solution (3.3), shaking well for each of added reagents, then heating in an electric furnace to boiling for 5-10 min, removing it and cooling, adding a small amount of ammonium persulfate (3.7), thermally oxidizing in the electric furnace until the purple red color of permanganic acid appears, boiling for another 5-8 min, removing it and cooling, adding 10 ml sodium chloride solution (3.9), allowing heating continued until no more small bubbles are generated, then removing it and cooling.

5.3.3 Adding 4 drops of o-anilinobenzoic acid indicator (3.8), titrating with ferrous standard solution (3.13) to the point where the solution changes from cherry red to bright green in color as the end point.

6. The calculation of the results:

The chromium content is calculated according to the following equation:

$$Cr(\%) = \frac{V \cdot c \times 0.01733}{m} \times 100\%$$

wherein:
V is the volume of ferrous standard solution consumed, ml;
c is the concentration of ferrous standard solution, mol/L;
m is sample weight, g; and
0.01733 is the mass of chromium equivalent to 1 ml of ferrous standard solution with a concentration of $c[FeSO_4 \cdot (NH_4)_2SO_4]=1.00$ mol/L.

7. Tolerance %

| Chromium content | tolerance |
|---|---|
| 0.10 to 1.00 | 0.05 |

However, in practical applications, this method has some problems: (A) a large amount of precipitate is generated during the redox process of the sample solution, the problems regarding to such precipitate are that: 1. it severely affects the determination of titration end point, leading to over-titration easily, thus the result is higher than real value, and the reproducibility is poor; 2. the precipitate adsorbs small amount of ions of the tested elements indefinitely, leading to a result lower than real value, and the reproducibility is poor; 3. part of vanadium co-precipitated into the precipitate, so it is difficult to completely eliminate the interference of vanadium to chromium, so the accuracy of the result of chromium is affected; 4. the sample solution is subjected to a prolonged heating during the oxidation-reduction, so the precipitate can easily jump and splash to cause the loss of the sample liquid, and re-measurement has to be done, in addition, to avoid this, an operator has to stand next to the heating furnace all the time and keep shaking the Erlenmeyer flask, thus the labor intensity is very great. (B) whether or not the excess oxidizing and reducing agents are consumed completely during the oxidation-reduction is purely determined according to the operator's experience, and if there is any left, the result will be affected significantly. and (C) the time for analysis is long, and the efficiency is low.

As the exact amounts of chromium and vanadium added will directly affect the quality of the downstream products of hard alloy, it is of realistic significance to overcome the shortcomings in the macroanalysis of chromium in a tungsten system by the classical redox titration mentioned above and provide a more accurate, fast and efficient analytical method.

SUMMARY OF THE INVENTION

An object of the present invention is to provide a method for determining chromium content in a tungsten matrix with added chromium or simultaneously added chromium and vanadium, which applies the method for determining chromium content by classical redox titration in a tungsten system and eliminates the precipitate generated in the process of oxidation-reduction, so the measurement can be carried out in a quite clear condition, and the interference from vanadium can be eliminated completely and quantitatively, thus the accuracy and speed of the determination of chromium content in a tungsten matrix with singly or simultaneously added chromium and vanadium are improved.

To this end, the present invention provides a method for determining chromium content in a tungsten matrix with singly or simultaneously added chromium and vanadium, characterized in that, a test sample is subjected to melting with sodium peroxide and hot water leaching; meanwhile said sodium peroxide is also used as an oxidizing agent to oxidize all the chromium to high valences; and the main body of tungsten is coordinated by ammonium hydrogen fluoride to prevent tungstic acid from precipitating; precipitation and turbidity are avoided throughout the analysis, so titration can be carried out in a quite clear condition with accurate and reliable results. The clearness of the solution when titrating is very important for the accuracy of titrimetric analysis; that the solution is always clear throughout the measurement ensures that the interference with determination of chromium from vanadium is accurately and quantitatively eliminated; the interference from vanadium is eliminated by subtraction method, titrating with ferrous ammonium sulfate standard solution after oxidation with potassium permanganate.

Instead of silver nitrate, ammonium persulfate, manganese salt, sodium chloride and other reagents, which are used in determining chromium content by classical redox titration, the present invention uses a complexing agent and an oxidizing agent to achieve an oxidation-reduction process successfully, while the solution is always clear throughout the measurement, and the mutual interference between chromium and vanadium can be accurately eliminated, so the determination accuracy is improved to a higher level, accurate, fast and reproducible results can be obtained. The reasons are as follows:

(A) Using ammonium hydrogen fluoride complex to coordinate with the main body of tungsten can prevent the precipitation of tungstenic acid during the acidification of the sample solution to produce tungstenic acid precipitate;

(B) An oxidizing agent, sodium peroxide, is used to complete the processes of melting sample and oxidizing chromium, this oxidizing agent allows the sample solution to be heated without producing any precipitate;

(C) A wider range of amount for complexes and oxidizing agents does not interfere with the measurement;

(D) The sample solution is always clear throughout the measurement, ensuring that the mutual interference between chromium and vanadium in the analysis can be eliminated quantitatively; accurate determination of chromium and vanadium content in a tungsten matrix with simultaneously added chromium and vanadium is achieved;

(E) Analytical cycle is greatly shortened, being only about one quarter of the time for the classical redox titrimetric analysis, so the working efficiency is greatly improved. The analytical process of the classic method is particularly time consuming, as the sample needs a long time for melting, later it needs repeated heating and cooling, and confirmation of the complete extermination of the excess oxidizing agent will also take times, so the processing time may be at least 3 or 5 hours or more, and if a re-measurement caused by the splashing and jumping of the precipitate is needed, it may take nearly one day, so the efficiency is very low. In the present invention, slight heating is needed for 3-5 minutes only when the leaching test solution melt lump cannot be leached out completely by warm water, afterwards the measurement is carried out in a cold state all the time, and there are no problems of splashing and jumping, the analysis takes only 50 minutes or so, so the efficiency is very high.

The present invention applies the determination of chromium by classical redox titration to the tungsten matrix by the optimization of the conditions for analysis to achieve the accurate determination of chromium and vanadium contents in a tungsten matrix with simultaneously added chromium and vanadium, the method is more accurate and reproducible than before the optimization of the conditions for analysis, and the time for analysis is much shorter. The measuring range of the method: Cr: 0.050-1.00%, V: 0.050-1.00%. The Relative error is less than 5%, which can fully satisfy the requirements of the products and processes for the determination.

Precipitation and turbidity are avoided throughout the analysis, titration can be carried out in a quite clear condition with accurate and reliable results. The clearness of the solution when titrating is very important for the accuracy of titrimetric analysis; the solution is always clear throughout the measurement, ensuring that the interference with determination of chromium from vanadium is accurately and quantitatively eliminated.

DETAILED DESCRIPTION OF THE INVENTION

The determination of chromium content in a tungsten matrix (such as tungsten carbide and the like) with singly or simultaneously added chromium and vanadium by redox titration is provided according to this invention.

1. Applicability:

This method is useful for determining chromium content in a tungsten matrix (such as tungsten carbide and the like) with singly added chromium or simultaneously added chromium and vanadium by redox titration. The measuring range is 0.05-1.00%.

2. Principle:

A test sample is subjected to melting with sodium peroxide and hot water leaching, the sodium peroxide is also used as an oxidizing agent to oxidize all the chromium to high valences, the main body of tungsten is coordinated by ammonium hydrogen fluoride, the alkaline solution is neutralized with sulfuric acid and is adjusted to an appropriate acidity, sodium diphenylaminesulfonate is used as an indicator, ferrous ammonium sulfate standard solution is used for titration. The interference from vanadium is eliminated by subtraction method, by means of titrating with ferrous ammonium sulfate after oxidation with potassium permanganate.

3. Reagent:

3.1 Sodium peroxide AR
3.2 Saturated ammonium hydrogen fluoride AR
3.3 Sulfuric acid AR, (1+1)
3.4 Phosphoric acid AR, ($\rho$1.68)
3.5 Potassium permanganate solution AR, (10 g/L)
3.6 Sodium nitrite solution AR, (100 g/L)
3.7 Sodium diphenylaminesulfonate solution AR, (10 g/L)
3.8 Chromium standard solution: AR, c ($\frac{1}{6}K_2Cr_2O_7$)=0.05 mol/L
3.9 Ferrous standard solution 3.9.1 Preparation: Weighing 60 g of ferrous ammonium sulfate to a 500 ml beaker, adding 350 ml of sulfuric acid (5+95) and stirring until being completely dissolved, filtering with a filter paper if the solution is turbid at this time, diluting with sulfuric acid (5+95) to 5000 ml and mixing well.

3.9.2 Calibration: Pipetting three aliquots of 20 ml chromium standard solution (3.8) into a 500 ml Erlenmeyer flask, diluting with water to about 100 ml, adding 15 ml mixture of sulfuric acid-phosphoric acid (1+1+5), adding two drops of sodium diphenylaminesulfonate solution (3.7), titrating with ferrous ammonium sulfate standard solution (3.9.1) to the point where the solution changes from purple red to bright green in color as the end-point.

Calculation: The standard concentration of the ferrous solution is calculated according to the following equation.

$$c[FeSO_4 \cdot (NH_4)_2SO_4] = \frac{c_1(1/6K_2Cr_2O_7) \cdot V_1}{V_2}$$

Wherein:
$c_1$ is the concentration of potassium dichromate standard solution, mol/L;
$V_1$ is the volume of potassium dichromate standard solution, mL; and
$V_2$ is the volume of ferrous ammonium sulfate solution consumed, mL.

Arithmetic mean value of the three calibrations is taken as the result.

4. Sample

Crushing in a mortar that does not change the composition of the sample and passing through screen meshes with hole diameter of 0.18 mm.

5. Analytical Procedure 5.1 Sample weight

Weighing 1-3 g of a sample being accurate to 0.0001 g.

5.2 Measurement 5.2.1 Placing the sample (5.1) in a 30 ml iron crucible, oxidizing it into tungsten trioxide by calcining in a muffle furnace at 750° C., taking it out and cooling, adding 4-7 g sodium peroxide (3.1) and stirring well, covering it with a few sodium peroxide (3.1), placing it in a muffle furnace at 700° C. and melting for 10 minutes, then taking it out and cooling.

5.2.2 Placing it into a 250 ml beaker containing 50 ml hot water pre-added, after melt lump leaching, cleaning the crucible with water, transferring into a 250 ml volumetric flask after the melt lump completely decomposes, diluting with water to volume and shaking well.

5.2.3 Dry filtering, sucking 100 ml solution into a 500 ml Erlenmeyer flask (in the case of also having vanadium mixed, taking two aliquots of 100 ml filtrate), adding saturated ammonium hydrogen fluoride solution (3.2) and shaking well, neutralizing with sulfuric acid solution (3.3) to neutral, adding 10 ml more and shaking well, adding 5 ml phosphoric acid (3.4) and shaking well, diluting with water to a volume of about 200 ml and cooling to room temperature.

5.2.4 Adding two drops of sodium diphenylaminesulfonate solution (3.7), titrating with ferrous ammonium sulfate standard solution (3.9) to the point where the solution changes from purple red to bright green in color as the end-point, the volume consumed being denoted by V1.

5.2.5 For a sample also having vanadium mixed, adding 10 ml saturated ammonium hydrogen fluoride solution (3.2) to another 100 ml filtrate and shaking well, neutralizing with sulfuric acid solution (3.3) to neutral, adding 10 ml more and shaking well, adding 5 ml phosphoric acid (3.4) and shaking well, diluting with water to a volume of about 200 ml and cooling to room temperature, adding V1 ml of ferrous ammonium sulfate standard solution (3.9) and fully shaking well, standing still for several minutes, adding potassium permanganate solution (3.5) dropwisely until a stable red color appears for several minutes, shaking while adding sodium nitrite solution (3.6) to the point where the red color fades away and adding one more drop, shaking well, adding two drops of sodium diphenylaminesulfonate solution (3.7), titrating with ferrous ammonium sulfate standard solution (3.9) to the point where the solution changes from purple red to bright green in color as the end-point, the volume consumed being denoted by V2.

6. The Calculation of the Results:

Calculating chromium content according to the following equation:

$$Cr(\%) = \frac{(V1 - V2) \cdot c[FeSO_4 \cdot (NH_4)_2SO_4] \times 0.01733}{m} \times 100\%$$

wherein:

V1 is the volume of ferrous standard solution consumed in titration in the case of singly added chromium, or the volume of ferrous standard solution consumed in titration by chromium and vanadium together in the case of simultaneously added chromium and vanadium, mL;

V2 is the volume of ferrous standard solution consumed in titration by vanadium in the case of simultaneously added chromium and vanadium, mL;

$c[FeSO_4 \cdot (NH_4)_2SO_4]$ is the concentration of ferrous standard solution, mol/L;

m is the sample weight, g;

0.01733 is the mass of chromium equivalent to 1 mL of ferrous standard solution with a concentration of $c[FeSO_4 \cdot (NH_4)_2SO_4]$=1.00 mol/L.

The invention claimed is:

1. A method for determining chromium content in a tungsten matrix comprising the steps of:
    melting a tungsten sample with an oxidizing agent to form an oxidized tungsten sample, the oxidizing agent being sodium peroxide,
    hot water leaching the oxidized tungsten sample,
    complexing the leached oxidized tungsten sample with a tungsten complexing agent to form a solution, the tungsten complexing agent being ammonium hydrogen fluoride, and
    titrating the solution to determine the chromium content.

2. The method of claim 1 wherein titrating further comprising the steps of:
    adding an indicator to the solution, and
    adding a standard solution to the solution with the indicator until completion of titrating.

3. The method of claim 2 wherein the indicator being sodium diphenylaminesulfonate.

4. The method of claim 2 wherein the standard solution being a ferrous ammonium sulfate solution.

5. The method of claim 1 wherein complexing further comprising the steps of:
    neutralizing the solution with an acid.

6. The method of claim 5 wherein the acid being a first acid and a second acid.

7. The method of claim 6 wherein the first acid being sulfuric acid.

8. The method of claim 6 wherein the second acid being phosphoric acid.

9. The method of claim 5 further comprising the steps of:
    if vanadium is present in the tungsten sample,
    after neutralizing with acid,
    mixing in a known volume of a ferrous ammonium sulfate solution, then
    mixing in a vanadium oxidizing agent until a stable color change is achieved, then
    mixing in a sodium nitrite solution until the color change is reversed.

10. The method of claim 9 wherein the vanadium oxidizing agent being potassium permanganate.

* * * * *